United States Patent
Coassin et al.

(10) Patent No.: US 6,660,233 B1
(45) Date of Patent: Dec. 9, 2003

(54) ANALYTICAL BIOCHEMISTRY SYSTEM WITH ROBOTICALLY CARRIED BIOARRAY

(75) Inventors: Peter J. Coassin, San Juan Capristrano; Jack D. McNeal, Long Beach; David B. Helphrey, Santa Ana, all of CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 08/586,116

(22) Filed: Jan. 16, 1996

(51) Int. Cl.[7] .................................................. B01L 9/00
(52) U.S. Cl. .......................................... 422/104; 422/63
(58) Field of Search .............................. 422/63, 67, 81, 422/100, 102, 104; 436/43, 44, 46, 49, 50, 54, 55, 63, 164, 165, 174; 73/864.01, 864.21, 864.22, 864.24, 864.25

(56) References Cited

U.S. PATENT DOCUMENTS

| | | | | |
|---|---|---|---|---|
| 4,225,410 A | * | 9/1980 | Pace | 204/195 R |
| 4,308,028 A | * | 12/1981 | Elkins | 23/230 B |
| 4,318,884 A | * | 3/1982 | Suzuki | 422/63 |
| 4,586,546 A | * | 5/1986 | Mezei et al. | 141/2 |
| 4,769,216 A | * | 9/1988 | Chandler et al. | 422/58 |
| 4,806,313 A | * | 2/1989 | Ebersole et al. | 422/61 |
| 4,857,273 A | | 8/1989 | Stewart | |
| 4,877,745 A | | 10/1989 | Hayes et al. | |
| 4,909,992 A | * | 3/1990 | Bjorkman | 422/100 |
| 5,079,170 A | * | 1/1992 | Rosman et al. | 436/178 |
| 5,139,743 A | | 8/1992 | Ishizaka et al. | |
| 5,143,066 A | | 9/1992 | Komives et al. | |
| 5,164,318 A | * | 11/1992 | Sato et al. | 435/288 |
| 5,171,537 A | * | 12/1992 | Wainwright et al. | 422/100 |
| 5,296,194 A | | 3/1994 | Igarashi | |
| 5,387,526 A | * | 2/1995 | Garner et al. | 436/169 |
| 5,401,469 A | | 3/1995 | Kobayashi et al. | |
| 5,437,979 A | | 8/1995 | Rampal et al. | |
| 5,478,526 A | * | 12/1995 | Sakai et al. | 422/81 |
| 5,512,248 A | * | 4/1996 | Van | 422/100 |

* cited by examiner

*Primary Examiner*—Lyle A. Alexander
(74) *Attorney, Agent, or Firm*—William H. May; D. David Hill; Sheldon & Mak

(57) ABSTRACT

A system for detecting the presence of a target biomolecule in a sample where there is a robotic arm to move a pipette adaptor to the desired reagent locations to facilitate the detection.

12 Claims, 10 Drawing Sheets

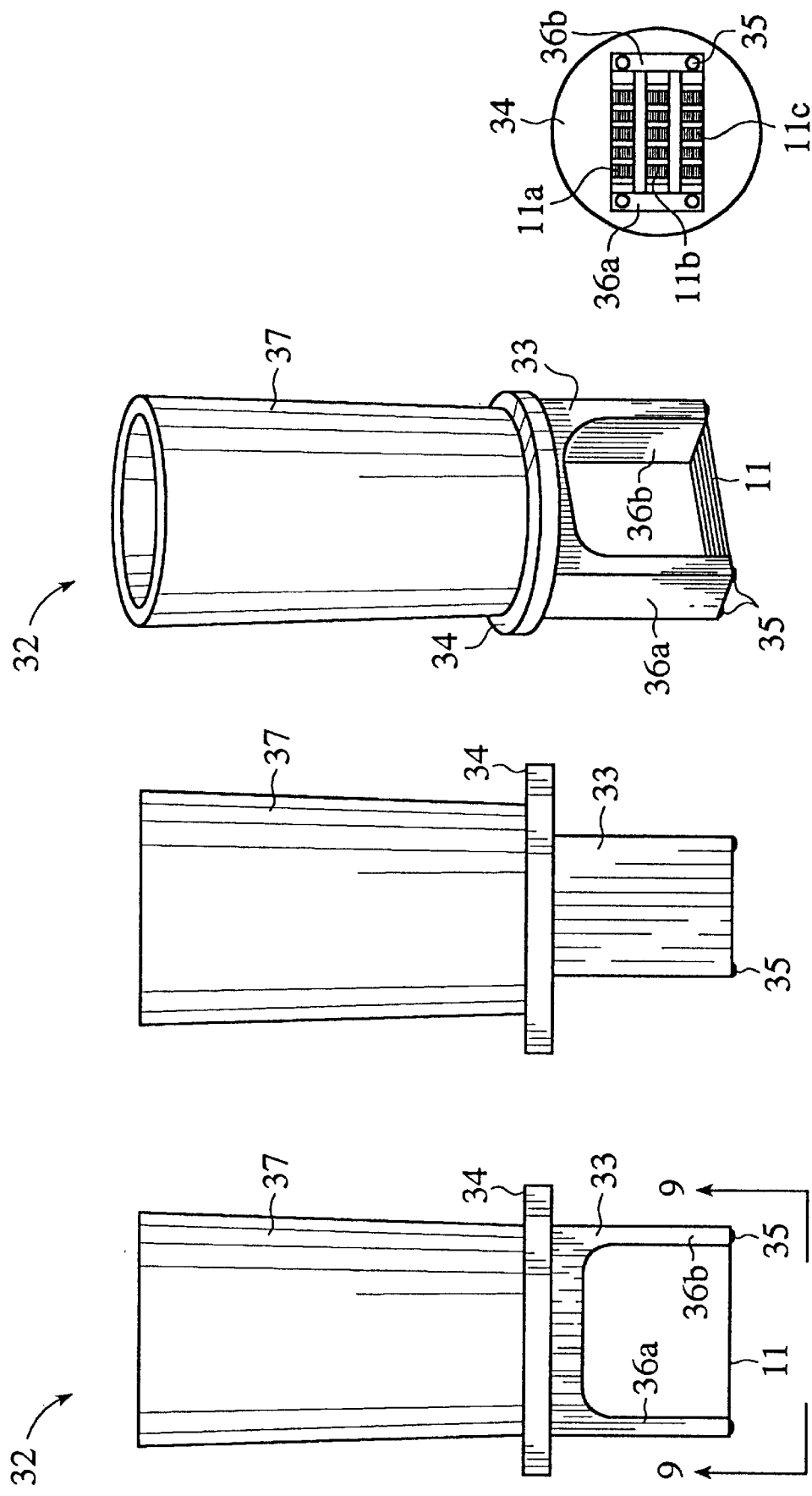

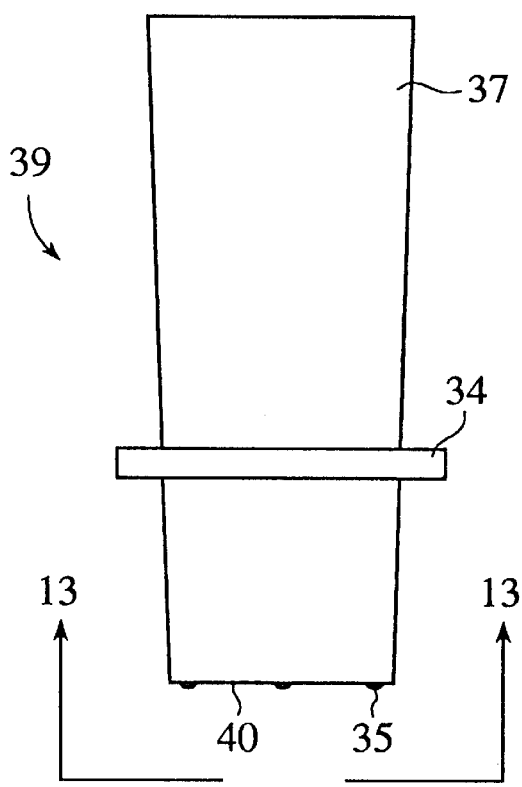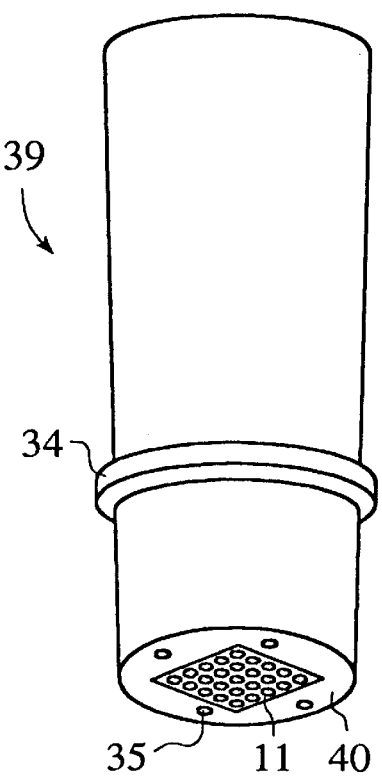
FIG. 11  FIG. 12
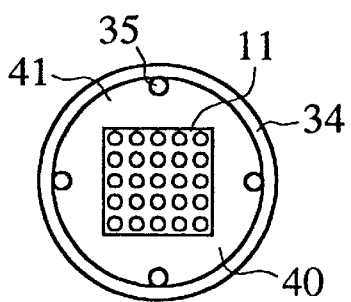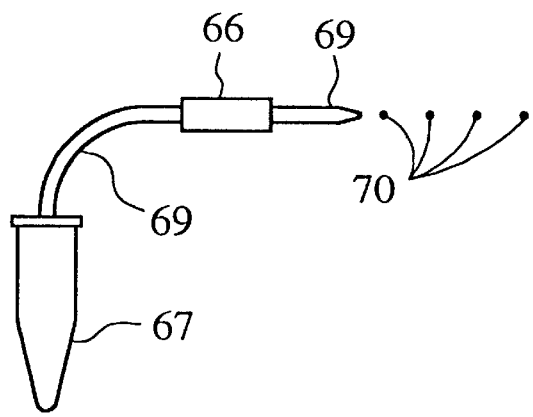
FIG. 13  FIG. 22

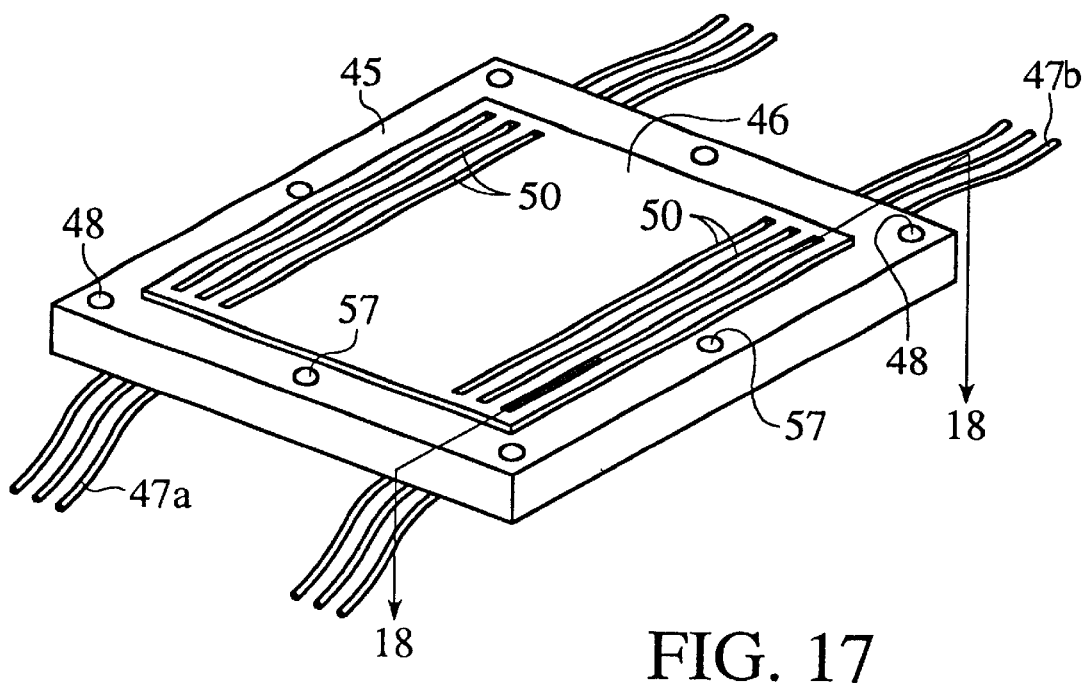
FIG. 17
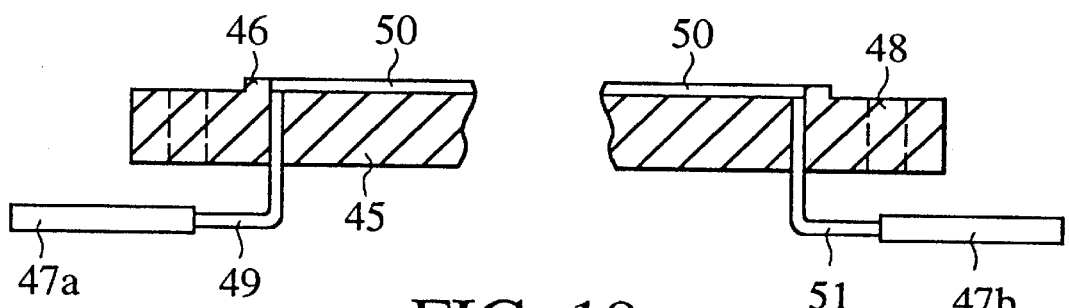
FIG. 18
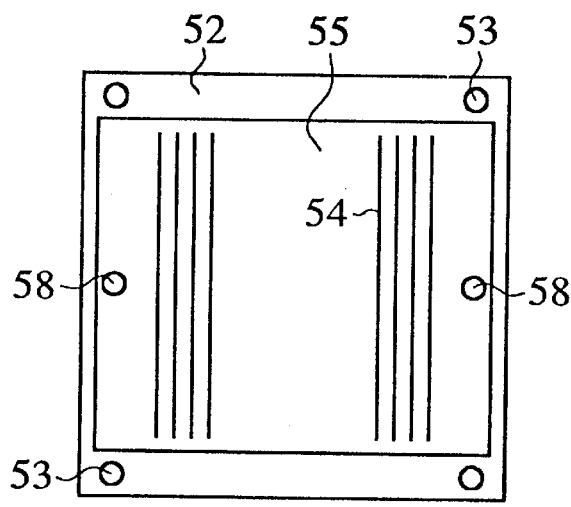  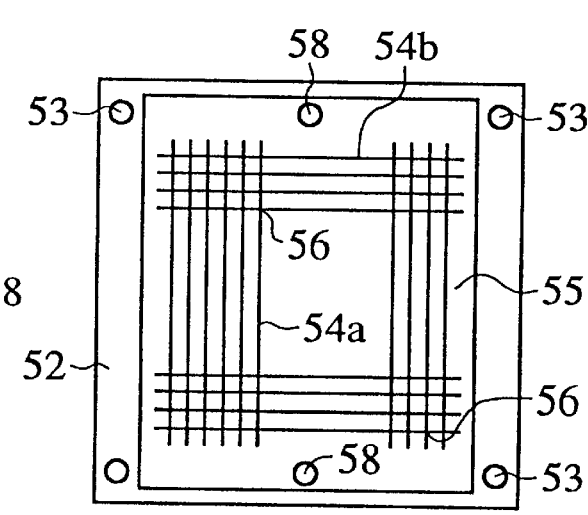
FIG. 19                FIG. 20

ANALYTICAL BIOCHEMISTRY SYSTEM WITH ROBOTICALLY CARRIED BIOARRAY

TECHNICAL FIELD

This invention relates to a system and methods for detecting the presence of target biomolecules within samples with robotic assistance for a sample holder carrying an array of reactants.

BACKGROUND ART

Assays for the detection of target biomolecules within a sample, especially of multiple target biomolecules within a sample, are often performed by applying a volume of the sample to a test slide, membrane, or other substrate having immobilized reactants which may interact with the target or targets to form detectable complexes. These immobilized reactants are usually disposed at fixed locations, with samples brought to these locations. U.S. Pat. No. 5,139,743, for example, discloses a. biochemical analysis apparatus wherein an applicator takes up a liquid sample and applies the sample to a fixed position test film for chemical analysis of the sample.

Sometimes complexes of target biomolecules and reactants are visually detectable directly after an appropriate incubation period for the sample and reactants, or after numerous development steps wherein development chemicals, such as fluorescent dye-conjugated molecules, are allowed to interact with the complexes. For example, the detection mechanism in U.S. Pat. No. 5,296,194 involves optically detecting a color change in a blood drop applied to a test slide.

U.S. Pat. No. 4,877,745 discloses methods for preparing immobilized reagents and applying samples to immobilized reagents. In particular, this patent discloses dispensing precisely controlled volumes of droplets onto a medium at precisely controlled locations, to form arrays of immobilized reagents by a jet head. An x-y plotter may be modified to carry a jet head so that reagent may be dispensed over an area.

Robotic laboratory workstations, such as the Biomek 1000 and 2000 of Beckman Instruments, Inc. have been developed for automatically carrying out assays involving multiple reactants and multiple samples. Typically such workstations are designed to deliver robotically precise volumes of reactants to a number of different samples located at known areas within the workstation. Alternatively, workstations can robotically move samples to reagents.

U.S. Pat. No. 5,171,537 to Wainwright et al. teaches activated immunodiagnostic pipette tips. The pipette tip houses a spherical element which is coated with a single ligand having affinity for a target molecule of a sample. With this device, the test element may be brought to contact the sample, as by aspirating the sample into the pipette tip. These pipette tips are limited in their sample throughput because they house only a single ligand reagent and thus preclude the detection of multiple analytes within a sample.

A class of devices known as optical biosensors, characterized by immobilized assay species within a supporter and a light collection device coupled to an optical waveguide, is also known. Optical biosensors may be used for detecting and quantifying the presence of specific species in test fluid samples, such as in clinical diagnostic reactions. For example, U.S. Pat. No. 4,857,273 discloses an optical biosensor for immunoassays and certain other reactions. Other examples, involving use of an optical fiber, are U.S. Pat. No. 5,143,066 and U.S. Pat. No. 5,401,469.

It is an object of the present invention to provide apparatus and methods for rapidly and automatically determining the presence of multiple target biomolecules in a single sample. It is another object of the present invention to provide analytical methods which require minimal sample volume and a minimal number of liquid transfers. It is a further object of the present invention to provide a device and system for rapid assessment of samples for target biomolecules which is readily adaptable to a variety of chemical and other detection schemes.

DISCLOSURE OF THE INVENTION

The present invention achieves the above objects by providing an analytical biochemistry system for automated analysis of samples for the presence of target biomolecules. The system includes a solid substrate which is supported by a holder and carried by a manipulator, such as a robotic arm. Immobilized on the solid substrate surface at discrete, site-specific locations are reactants in an array which are capable of binding with target biomolecules in specific binding reactions to form immobilized biomolecule complexes. Such an array is termed a "bioarray". The presence of target biomolecules in the sample is determined by detecting immobilized biomolecule complexes on the bioarray with some kind of probe, e.g. a fluorescence detector. In operation, the manipulator moves the bioarray to contact the substrate surface with a volume of sample. Then the manipulator moves the contacted bioarray to a detection station to detect the absence or presence of immobilized biomolecule complexes. In alternative embodiments the bioarray is stationary and a sample manipulator moves samples to the holder.

In the preferred embodiment, the bioarray is mobile, being carried by a manipulator. A detection station is located near the sample to probe the substrate after interaction between the reactants and sample or samples has occurred.

Distinct reactants specific to different target biomolecules are immobilized on a preferably flat, nonporous substrate. These reactants form a plurality of active sites on the substrate at known locations. The substrate may be a planar strip with linearly-arranged reactants forming separable spots or bands, or may be a planar sheet having an area-wide arrangement of reactants, forming spots or dots in a two-dimensional array, or may be a fiber or rod with substrate disposed in a manner similar to a strip.

The holder supports the bioarray and is carried by the manipulator which transports the substrate to the location of the fixed sample, and then to the location of the detection assembly. As stated, the substrate could be fixed and the sample transported. One example of a holder is a pipette or a pipette tip, within which a bioarray is affixed. The sample is drawn up into the pipette tip, as with aspiration from a bulb or vacuum pump, or withdrawal of a plunger. The sample is thus placed in contact with the substrate, allowing any target molecules which may be present within the sample to interact with the appropriate reactive sites on the substrate. After the appropriate incubation or reaction period, the sample may be removed from the pipette tip, as by air pressure or positive displacement with a plunger.

Another example of a useful holder is a pipette adapter resembling a truncated pipette tip and having a bracket or a flat surface for supporting the substrate. The pipette adapter may be placed directly into a sample, such as in a well of a microtiter plate or in a vial, in order to provide contact of the holder and the sample. The pipette adapter and accompanying substrate are then removed from the sample to a detector station. The various holders of the present invention may be adaptations of standard pipetting tools. The holders also are designed to require minimal sample volumes and to allow optical inspection of the substrate with minimal interference by the holder.

The method for detecting target biomolecules within a sample includes the steps of treating a substrate with a plurality of distinct reactants to form reagents immobilized on the substrate at fixed, known positions defining an array, i.e. a bioarray. The reactants are selected to bind one or more target molecules to form a complex having a detectable and identifiable characteristic, such as a fluorescent signature. The bioarray is supported in the holder. In turn, the holder has a shape which can be picked up by a manipulator which moves the substrate for contact with the fixed sample, and then removes and possibly rinses the substrate at another location to remove unbound biomolecules. Then the manipulator moves the substrate to a probing station, such as an optical inspection location for probing the active sites of the substrate with a beam for determining complementation of the target biomolecules by detecting the optically detectable characteristic.

Inspection may include detection of fluorescence, light scattering, absorbance, reflectance, chemiluminescence, radioactive emission, conductivity or electronic property. Depending on the nature of the substrate, detection of transmitted light is also possible. Prior to probing, intermediary steps to enhance visualization or realization of complementation, such as treatment with development chemicals, fluorescent dyes, etc. may be desired. Optical inspection of the substrate within the pipette tip is possible by use of an optical surface on the pipette tip. Optical inspection on the pipette adapter is unencumbered.

A manipulator in the form of a robotic arm gripping the pipette tip or pipette adapter type of substrate holder may place the bioarray in contact with the sample, and subsequently transfer the substrate to a detection assembly. Multiple sample transfers are thus eliminated. A computer controlling the robotic arm movement, the incubation times, and providing further analysis or display of detected signals from the substrate is preferred. An automated instrument includes a detection assembly, which in one embodiment includes a laser source providing an excitation beam to impinge upon the active sites of the substrate, a light collector for gathering signals emitted from the substrate, and a detector, such as a photomultiplier tube or CCD array. Alternatively, it may have multiple detection assemblies, depending on the requirements of the sample and the substrate chemistries. Relative movement of an excitation beam and the bioarray may be provided by the robotic arm holding the substrate or by scanning optics, such as a galvo mirror, within the excitation path of the detection assembly.

A substrate intended for use in the present invention may be an oligonucleotide array, a peptide array, or an immunochemical array, among others, and may be created on a separate member, such as a small slide, and affixed to the holder, or it may be created directly on the holder. Creation of the bioarray may be via biopolymer synthesis on a solid phase member or deposition of reactants, e.g. by movable nozzles, such as the type used for ink jet printing, or by some other method. The reactants may be affixed to the member via specific or nonspecific covalent linkages, physical adsorption, or some other form of adhesion. The interaction or complexing of the target biomolecules and the immobilized reactants may be by affinity linkages, ionic linkages, adsorption, or some other reasonably secure manner.

The present invention provides a simple, highly adaptable method and apparatus for quickly and easily assessing samples for the presence of biomolecules.

BRIEF DESCRIPTION OF THE DRAWINGS

FIG. 6 is a front view of a pipette adapter with bracket for use in the system of FIG. 1.

FIG. 7 is a side view of the pipette adapter of FIG. 6.

FIG. 8 is a perspective view of a pipette adapter, supporting a substrate for use in the system of FIG. 1.

FIG. 9 is an end view of the pipette adapter of FIG. 8, showing details of the supported substrate.

FIG. 11 is a front view of a flat bottom pipette adapter for use in the system of FIG. 1.

FIG. 12 is a perspective view of the flat bottom pipette adapter of FIG. 11, showing a substrate at the base of the adapter.

FIG. 13 is an end view of a flat bottom pipette adapter of FIG. 11, showing details of the substrate.

FIG. 17 is a perspective view of a device which may be utilized for biopolymer synthesis on a substrate to create a substrate in accord with the present invention.

FIG. 18 presents a cross sectional view of the device of FIG. 17.

FIG. 19 is a plan view of a substrate and backing plate for biopolymer synthesis, showing a one-dimensional biopolymer array for a substrate in accord with the present invention.

FIG. 20 is a plan view of a substrate and backing plate, showing two-dimensional biopolymer synthesis for a substrate in accord with the present invention.

FIG. 22 is a plan view of the internal elements of a jet head of FIG. 21.

Best Mode for Carrying Out the Invention

Figure 1:
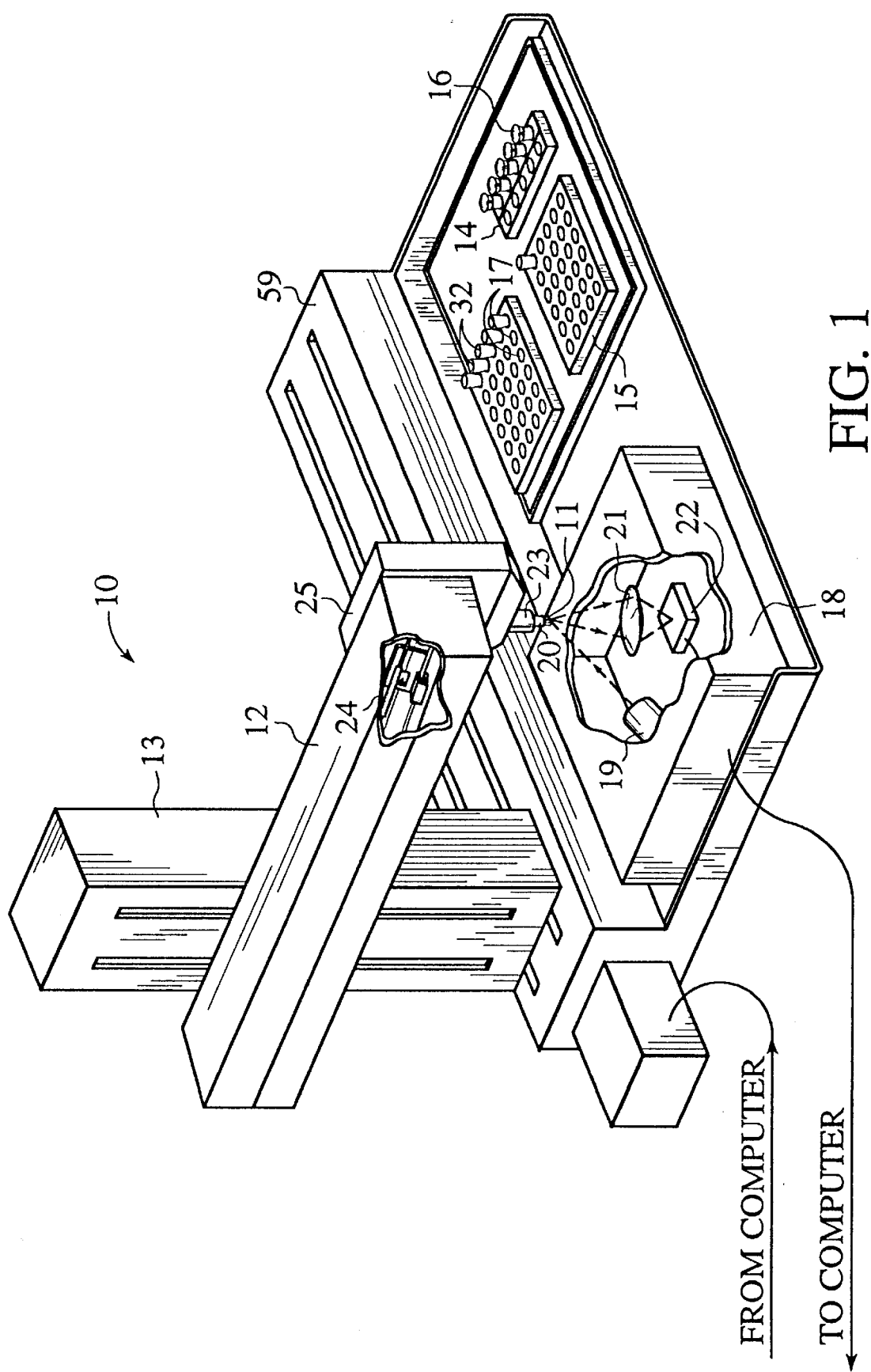
FIG. 1 is a perspective view of an automated instrument for performing the target biomolecule detection in accord with the system of the present invention.

With reference to FIG. 1, a system 10 utilizing a movable bioarray is shown. Specifically, a robotic arm 12 carries a holder 20 which fits and transports bioarray 11, first to the sample, which may be in well 17 of microtiter plate 15 or in vial 16 of rack 14. Although a robotic arm is one form of manipulator which may be used, other simpler manipulators may be employed, such as mechanical movements. A preferred type of manipulator device is the Biomek, a trademark for an instrument of Beckman Instruments, Inc. As will be seen below, the substrate portion of bioarray 11 is mounted in a holder having a support region which may be quite small. After the bioarray and the sample have had a sufficient incubation or reaction time for interaction of reactants on the substrate and any target biomolecules which may be present within the sample, the robotic arm 12 moves the substrate 11 to the detection assembly 18 of instrument 10.

In FIG. 1, optical detection station 18 is presented in a cutaway view showing laser 19, light collector 21, and detector 22. Both the detection station 18 and the robotic arm 12 may be attached to a computer, not shown, which generates commands for movement of the robotic arm and receives signals from the detection assembly which may, in turn, be analyzed to determine whether a specific target biomolecule is present and which may be displayed. The substrate itself is held within a holder 20 which may be coupled to the cantilevered robotic arm 12 via pick-up shaft 23 or by some other coupling method. Tracks in the tower 13, the arm 12, and base 59 of the instrument 10, as well as controls 24 within the robotic arm 12, position the pick-up unit 25 relative to the samples and the detection assembly 18 with x,y,z motion, i.e. three degrees of freedom. A wide range of motion is available over a base the size of a desktop. Many sample wells may be reached as well as many substrate holders having treated substrates or untreated substrates which may be treated by motion to a nearby location where reactants may be sprayed or otherwise applied to the substrate.

Figure 2:
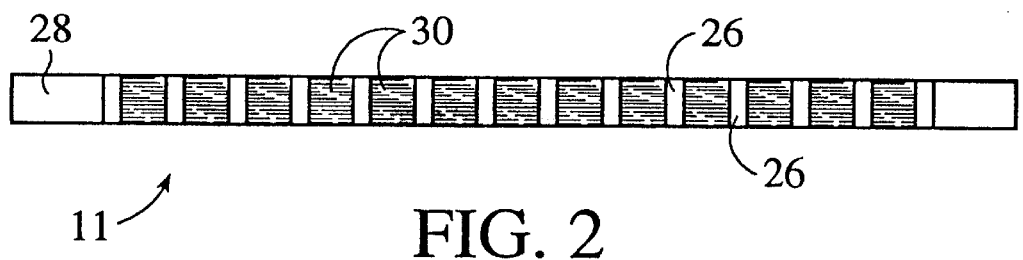
FIG. 2 is a plan view of a linearly-arranged substrate for use in the system of FIG. 1.
Figure 3:
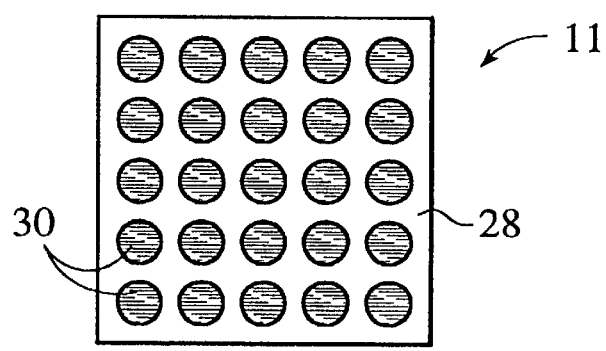
FIG. 3 is a plan view of a two-dimensional substrate for use in the system of FIG. 1.

FIG. 2 presents a linearly-arranged, flat substrate as a support portion of a bioarray, with active sites 30 forming bands along substrate 28 which is shaped as a strip. Spaces 26 are provided to place the plurality of active sites 30 in a spaced-apart relation along substrate 28. In FIG. 3, an area-wide treated substrate is created by positioning the active sites in a two-dimensional relation on a planar sheet substrate. Active sites 30 are positioned in spaced-apart relation on substrate 28, as before. As illustrated in FIGS. 2 and 3, the active sites 30 may be bands, as in FIG. 2, or spots, as in FIG. 3, or some other shape. The spots are in known locations and are specific for a target biomolecule. A plurality of linear substrates of FIG. 2 may also be arranged in parallel to create a two-dimensional bioarray.

The size of the substrate is typically a few centimeters on a side, but could be smaller or larger.

By way of example, the reactants forming the active sites may comprise complementary DNA strands for detection by DNA hybridization or they may comprise immunological biomolecules for detection by immunological complexing, such as formation of antigen-antibody complexes.

Figure 4:
FIG. 4 is a plan view of a pipette tip having a substrate for use in the system of FIG. 1.

The device of FIG. 4 represents one example of a substrate holder which may be used to present the bioarray to the sample. A pipette tip 27 is shown with a substrate 11 supported longitudinally along an inside wall. The substrate is preferably positioned along an inside wall of the pipette tip and the pipette tip is comprised of an optical glass or plastic allowing optical inspection of the substrate while the substrate is positioned inside the pipette tip. The sample is drawn into the pipette tip by aspiration and allowed to interact with substrate 11. Pipette tip 27 preferably has at least one flat surface, i.e. the surface opposite the substrate, for accurate optical inspections. This feature and a narrow bore also help minimize the amount of sample necessary and place the sample and substrate in close proximity. The pipette tip 27 may be used in conjunction with a rubber bulb, vacuum pump, robotic pipettor as in FIG. 1, or other device. The term "pipette tip" is meant to include pipettes, such as long cylindrical glass or plastic pipettes which are designed to operate in connection with a simple suction device.

Figure 5:
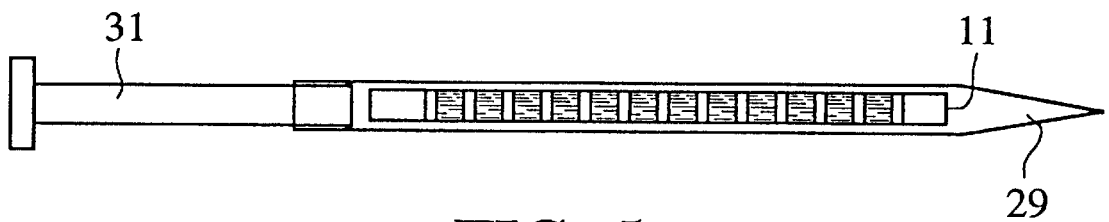
FIG. 5 is a plan view of a plunger-type pipette tip having a substrate for use in the system of FIG. 1.

FIG. 5 shows a second embodiment of a substrate holder wherein the substrate 11 is housed within a plunger-type pipette tip, in the same manner as the FIG. 4 embodiment. Pipette tip 29 also has a narrow bore and flattened surface. The sample is drawn into the plunger-type pipette tip 29 through withdrawal of plunger 31. Positive displacement of the sample is used to eject the sample from the pipette, as by depression of plunger 31 or by some other fluid manipulation. The embodiment of FIG. 5 has an advantage over the embodiment of FIG. 4 in that the sample does not drain from the pipette tip when the pipette tip of FIG. 5 is detached from a pipetting tool.

In FIGS. 6–9, a substrate holder takes the form of a pipette adapter 32 characterized by a bracket 33 at one end. The bracket has opposed prongs 36a–b, easily visible in FIG. 8, which support the ends of the substrate which is part of the bioarray. The opposite end of the bracketed pipette adapter preferably has a coupler 37 for joining a robotic or standard pipetting tool.

In FIG. 8, the coupler 37 is depicted as a hollow cone which may fit the conical shaft of a robotic or standard pipetting tool with an appropriate securing mechanism, such as a friction fit, with provision for ejection of the adapter for use. Many different types of couplers may be used, however. Of course, the pipette adapter 32 need not have any coupler, but it is preferred that the adapter have a gripper or other means for manipulating the adapter so, for example, the adapter may be moved into and out of sample wells easily.

Figure 10:
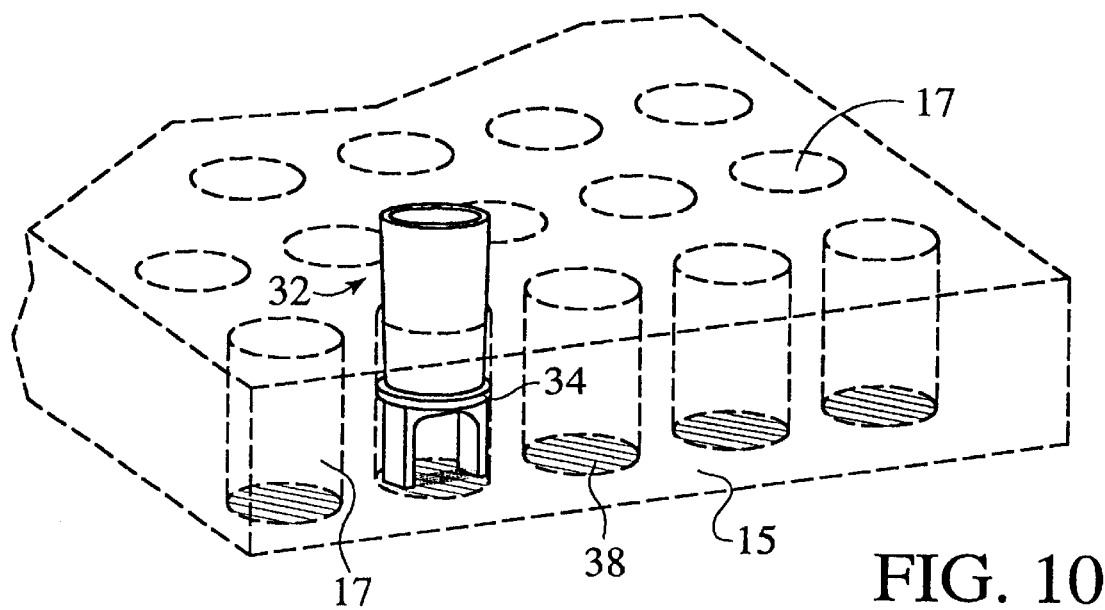
FIG. 10 is a plan view of a pipette adapter positioned within the sample well of a microtiter plate.

The bioarray is preferably oriented so that the active sites face downward. Thus, when the adapter is placed within a sample well, as in FIG. 10, contact of the active sites of the substrate and the sample is facilitated. Pipette adapter 32 is preferably equipped with knobs 35 on the prongs of the bracket, visible in FIGS. 6–9. These knobs position the substrate slightly above the bottom of the sample well, and protect the treated substrate from physical abrasion and contamination. Without such knobs, placement of the adapter into the well may press the substrate so close to the bottom of the well as to exclude sample from the face of the substrate, preventing proper contact and interaction of the sample and the substrate. Bracketed pipette adapter 32 also preferably contains a ring or disk-shaped evaporation barrier 34 which is disposed about the midsection of the adapter, or at the base of the bracket portion. Because some samples may easily evaporate, evaporation barrier 34 is preferably provided to protect the sample during the substrate and sample incubation period. In FIG. 10, evaporation ring 34 is seen providing a barrier when pipette adapter 32 is inserted into well 17, thus limiting the exposure of sample 38. The diameter of pipette adapter 32, and particularly bracket 33, is sufficiently narrow in order to easily fit within the microtiter plate's well, as also seen in FIG. 10.

FIG. 9 presents an end view of the bracketed pipette adapter 32. This view is indicated by axis 9–9 of FIG. 6, viewed in the direction of the arrows. From the end view, the substrate 11 is more clearly visible in its preferred downward facing orientation. The substrate of FIG. 9 is in a linearly arranged, but segmented, form. Thus strips 11a, 11b, and 11c are positioned in a generally parallel arrangement and secured by prongs 36a–b of the bracket 33. The nature and shape of the substrate may be easily adapted to sample, applicator, and space considerations. The two-dimensional substrate of FIG. 3 would adapt easily to bracketed pipette adapter 32. The substrate is held by prongs 36a-b by adhesion, welding, clamping, or any other means for gripping which will not interfere with the testing of the sample. In the end view of FIG. 9, evaporation disk 34 is visible beyond the prongs and the substrate.

In FIGS. 11–13, a flat-bottom pipette adapter 39 is utilized to support and transport the bioarray. Flat-bottom pipette adapter 39 has a flat bottom surface 40, visible in FIG. 12, and may have a coupler 37 at an end opposite to the flat bottom surface 40 for fitting the adapter to pipetting tools or a robotic arm, as in the bracketed pipette adapter embodiment. Similarly, flat bottom pipette adapter 39 may have a simple means for manually gripping the pipette adapter and applying the substrate 11 to the sample. Also, as with the bracketed pipette adapter 32, the flat bottom adapter 39 is preferably outfitted with knobs 35 and evaporation ring 34.

In FIG. 13, the substrate 11 is seen to be a two-dimensional array of spots or dots, as in FIG. 3. Evaporation ring 34 is visible in this view, taken along axis 13–13 of FIG. 11, and situated beyond flat bottom surface 40.

Figure 14:
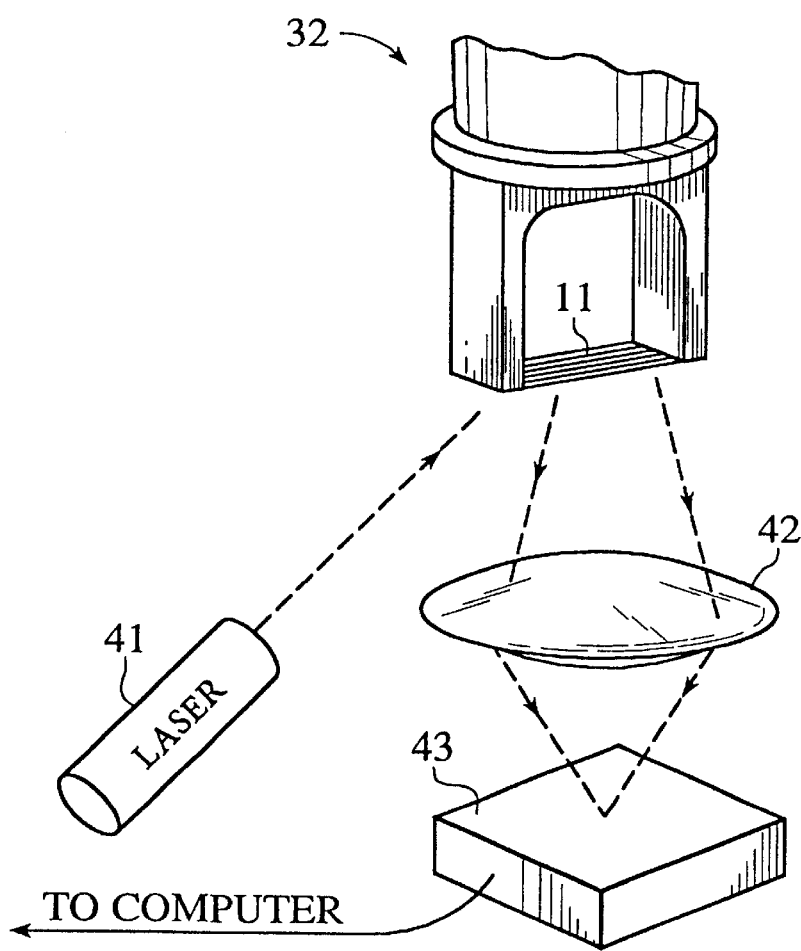
FIG. 14 is a perspective view of the elements of an optical detection station for use in the system of FIG. 1.

In FIG. 14, details of the internal elements of a biomolecule probe station are shown. Although various probe methods are available, the optical detection station 18 is an example. The station may be part of an analysis machine having a robotic arm, such as that shown in FIG. 1.

The robotic arm, pipetting tool, or other substrate holder positions the substrate, after it has interacted with the sample, in the path of a laser beam. Laser 41 creates a beam which impinges upon the active sites of the substrate 11, which is held within bracketed pipette adapter 32. The wavelength of the beam is selected to cause the return of a radiation signature from target molecules bound to the substrate. Such a signature comes from an optically detectable characteristic radiation pattern of the bound target molecules when excited by radiation of the beam, such as a characteristic band of fluorescent wavelengths. Time gated fluorescence, or other optical signal enhancement techniques, may optionally be used. The incident beam from the laser is scanned across the active sites of the treated substrate by relative motion of the substrate and the beam. Light emitted from the active sites is collected by light collector 42 and directed to detector 43, which may be a photomultiplier tube, CCD array, or other detection device, and which is preferably associated with a computer for any further analysis or display of the signals received from the substrate. Additional optical elements, such as wavelength selective filters, may be disposed in either the incident beam or the return light, as required by the characteristic radiation signature. Scanning may be accomplished by moving the substrate relative to the laser beam, by utilizing a scanning reflector such as a galvo mirror or polygonal mirror, or by some other well known means. Alternatively, the area of the laser beam may be expanded such that the entire area of the array is illuminated simultaneously, and scanning is not required.

The bioarray is optically probed by the beam for determining the extent of complexing of the reactants in the active sites of the substrate with target biomolecules in the sample. The optical inspection may be for fluorescent signals, reflectance, absorbance, light scattering, or chemiluminescence, among others. Details of the optical system may vary according to the nature of the signal to be detected. FIG. 14 illustrates a substrate 11 within bracketed pipette adapter 32 and facing in a downward orientation for impingement by the laser beam. This arrangement of the elements of the detection assembly is presented as an example of the arrangement of the detection assembly 18 of FIG. 1. In either case, the robotic arm may easily move the substrate and the associated bracketed pipette adapter to the detection assembly after the appropriate sample incubation period. The robotic arm may, however, be capable of moving the substrate so that it is oriented vertically, or in some other manner, relative to the laser beam. Also, the laser source for the excitation path may be positioned in a manner other than shown in order to impinge upon the substrate. Optical fibers may be employed to direct the beam or the return signal.

Figure 15:
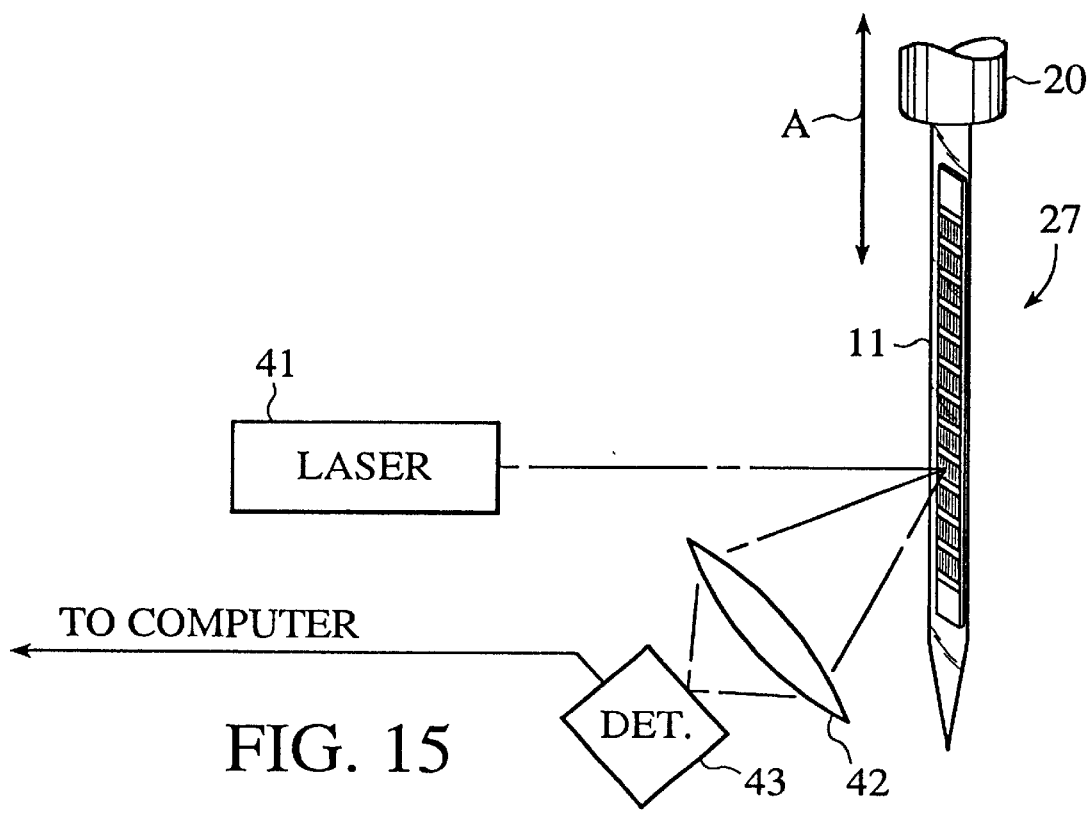
FIG. 15 is a plan view of an alternate embodiment of the detection station for use in the system of FIG. 1.

FIG. 15 presents a detection arrangement for probing of a substrate within a pipette tip. Pipette tip 27 has an optical surface so as not to interfere with the optical inspection. As with the bracketed pipette adapter, laser 41 impinges upon the substrate 11 and emitted signals from the substrate are gathered by light collector 42 and directed to detector 43 where the signals may be sent onto 15a computer for further analysis. The excitation beam from the laser impinges on the substrate through the wall of the pipette tip.

Figure 16:
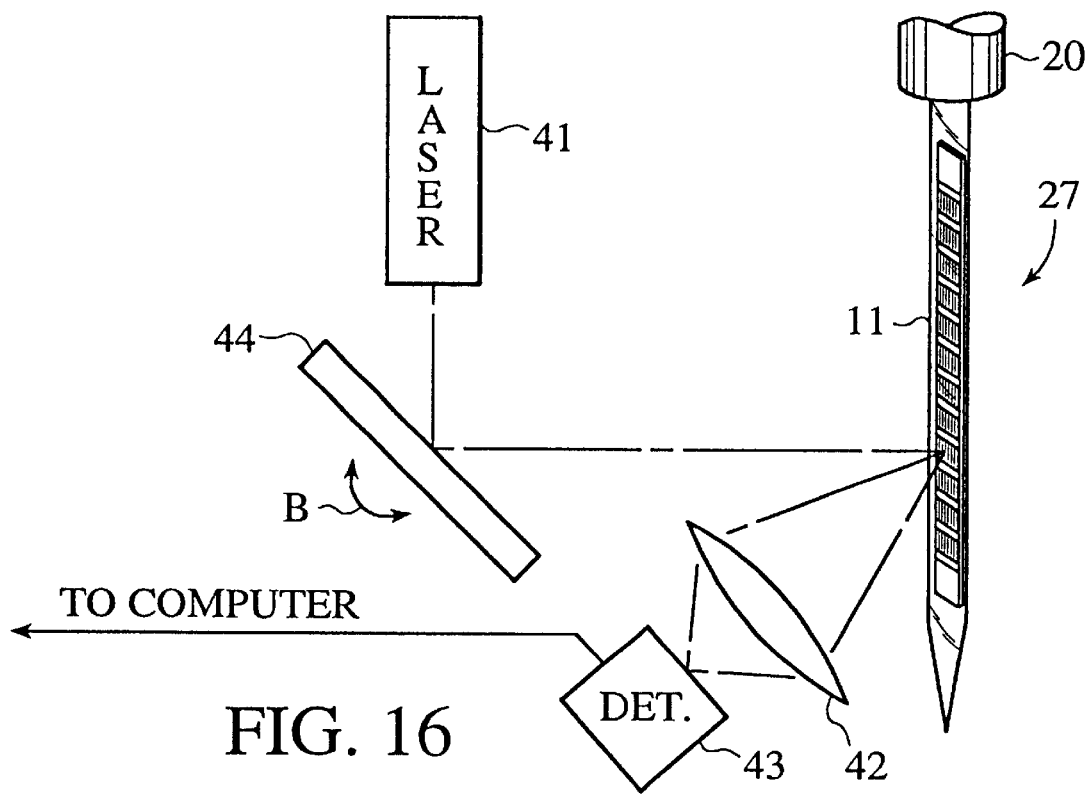
FIG. 16 presents yet another alternate embodiment of the detection station for use in the system of FIG. 1.

Arrow A of FIG. 15 indicates one example of how the substrate may be scanned, i.e. by providing a vertical motion to the pipette tip, via the robotic arm or some other mechanism. In FIG. 16, the substrate 11 within pipette tip 27 is scanned by the incident laser beam through the action of a scanning reflector 44, which may be rotated in direction B to cause scanning of the substrate 11. An automated apparatus such as instrument 10 of FIG. 1 may have a plurality of detection assemblies to which the robotic arm may move the substrate for reading, depending upon the type of manipulator used for the substrate, the type of signals to be read from the substrate, and the nature of the substrate and target biomolecules thereon.

The substrate may be formed by the device shown in FIGS. 17–20, which allows biopolymer synthesis on a solid support. The substrate may be used directly, or the biopolymers created by the device may be cleaved from the substrate and affixed to another substrate in any desired format. The method and apparatus depicted in FIGS. 17–20 are the subject of commonly-assigned U.S. Pat. No. 5,429,807, which is incorporated herein by reference. The device of FIG. 17 presents a synthesis device 45 which is a thick block having a plate surface 46 within which are a plurality of grooves or channels 50. Channels 50 are connected to tubing 47 at the underside of block 45 for flowing reagents through channels 50. The cross sectional view of FIG. 18, taken along axis 18–18 of FIG. 17, more clearly illustrates the reagent flow through the block wherein tubing 47a is connected to an inlet tubing connector 49 which communicates with channel 50. Tubing 47b communicates with outlet tubing connector 52 which in turn communicates with channel 50. Thus, reagents may be caused to flow through any of the channels 50.

To perform a synthesis, a solid support material, such as a sheet of activated polypropylene, may be placed on top of the channels of the block. A backing plate may be used to sandwich the polypropylene substrate, allowing the flexible polypropylene to seal against the channels 50 of the block 45. The backing plate 52 of FIGS. 19 and 20 may have holes 53 which may be aligned with holes 48 of block 45. The backing plate and the block may then be secured to one another. Synthesis or biopolymerization may be performed by activating the surface of the substrate, if necessary, and by flowing reagents through the channels, to cause formation of strands of biopolymers anchored to the substrate. This results in a one-dimensional array of biopolymers 54, as seen in FIG. 19. If desired, the block may be repositioned with respect to the substrate 55 and the process repeated. In FIG. 20, one-dimensional arrays 54a–b are presented in 90° offset orientations. The areas of overlap 56 provide new biopolymers having elements of each one-dimensional array 54a-b. Indexing pins 58, visible in FIGS. 19 and 20, may be utilized to position the substrate 55 in relation to the applicator. Indexing pins 58 mate with holes 57 in block 45. The resulting arrays may be utilized as is, or may be cleaved from the polypropylene substrate 55 and affixed to some other support. Additionally, the substrate 55 having the arrays may be segmented and attached to substrate 28, in the manner of FIGS. 8 and 9. Although channels 50 are illustrated, cavities for reagent flow having some other shape may be used. Although polypropylene is presented in the above discussion, other substrates such as glass, Pyrex, silicon, polystyrene, etc. may be utilized as supports for synthesis, as suggested in PCT application No. WO 93/09668.

Figure 21:
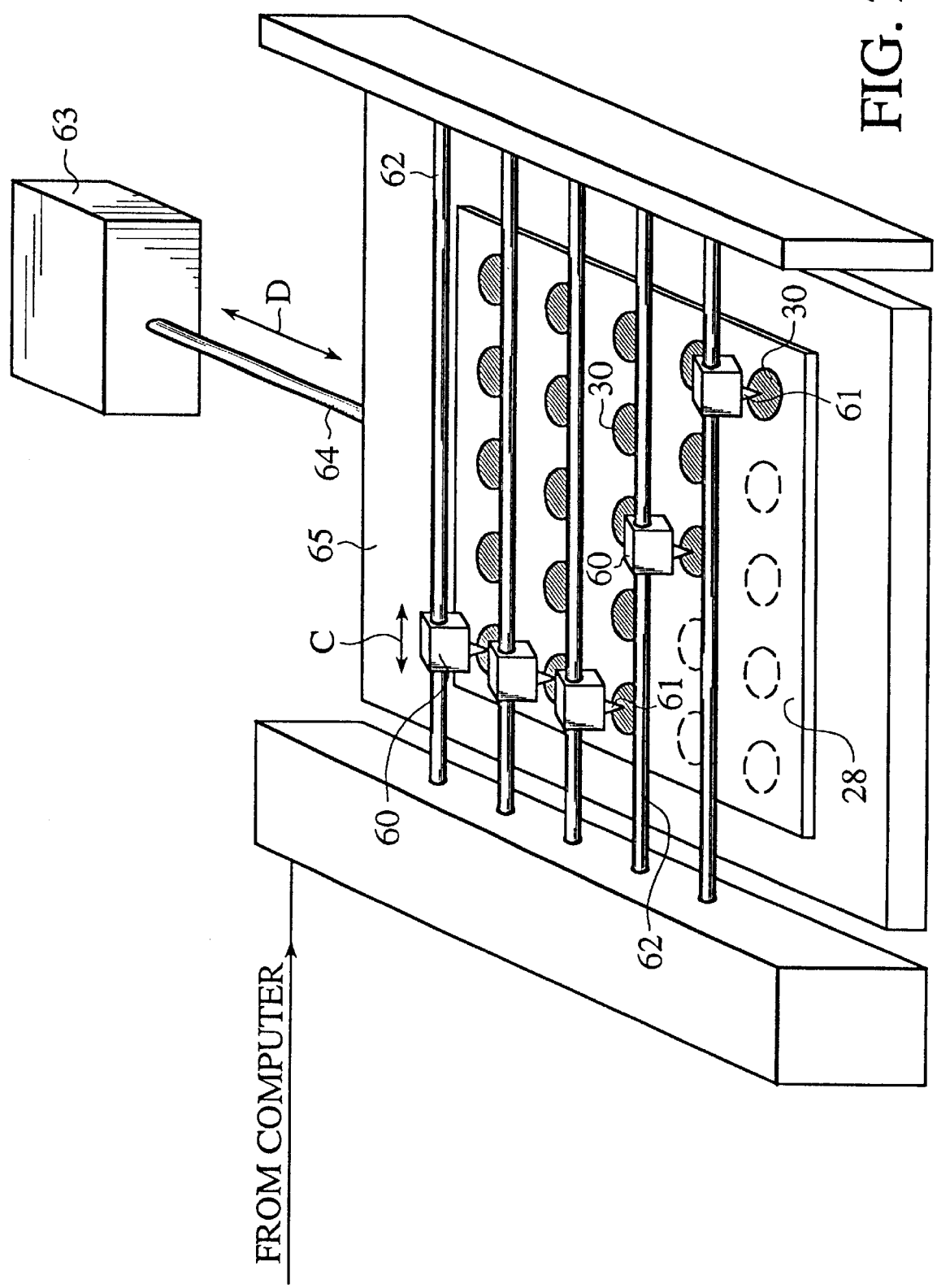
FIG. 21 is a perspective view of a jet head-type reagent deposition apparatus for creating a substrate in accord with the present invention.

With reference to FIG. 21, another method of creating a substrate is shown, utilizing movable nozzles. A support 28 is positioned on support frame 65 within a spray station. A plurality of ink jet-type heads 60 with nozzles 61 at the spray station are used to selectively deposit reactants on support 28 to create the plurality of active sites. Such heads are well-known in the field of ink jet printing. In the present invention, such heads are adapted for dispensing the reactants onto the desired locations of the substrate. If necessary, the substrate may be activated to receive and immobilize the reactants.

In FIG. 21, a plurality of different jet heads 60, each having a nozzle 61, may be moved on respective rails 62 in the direction indicated by arrow C. Each of the jet heads 60 dispenses a different reactant. Motion control of the jet heads 60 along rails 62 may be provided by a computer. The array may be moved by an actuator 63, which causes an arm 64 to move support frame 65 carrying the support 28. The actuator 63 may be a linear motor similar to that used to move magnetic heads in disc drives. In the situation where the substrate for the treated substrate is a strip, fixed position jet heads may be desired.

FIG. 22 illustrates a typical ink jet-type dispensing head as applied in this invention. Reactant contained in reservoir 67 passes through supply tube 69 to piezoelectric pumping chamber 66, and through chamber 66 to nozzle 69. Electrical pulses applied to pumping chamber 66 cause it to expand and contract in volume. Each time a pulse is applied and removed, this expansion and contraction event ejects a droplet 70 of reactant from the nozzle. Additional details of the design and operation of such a reactant dispensing device are disclosed in previously referenced U.S. Pat. No. 4,877,745. In addition to dispensing reactants, such a dispensing head might be employed to dispense ink or dye onto the substrate to form barcode patterns for machine reading of the identification of a bioarray.

Another method of preparing the bioarray is by a technique analogous to a printing method. In this technique an analyte is deposited on a substrate by stamping or embossing a very thin layer with an array of analyte spots at desired locations. For example, an antigen attached to a molecule anchored to the substrate by pressure contact will combine with an appropriate antibody associated with a specific target biomolecule. The antibody may be fluorescent for optical detection.

Other methods of preparing the substrate may be used, particularly photolithographic techniques. In a journal article entitled "Light-Directed, Spatially Addressable Parallel Chemical Synthesis" by S. Fodor et al. in Science, Feb. 15, 1991, p. 767, the authors describe a method of synthesizing complex compounds at spatially discrete locations defined by photomasks of the type used in the semiconductor industry. Molecular building blocks are deposited at desired locations by exposing underlying building blocks, i.e. "deprotecting" the underlying block for a reaction with the superposed building block. Successive building blocks are added until a desired compound is formed. The location of each compound is precisely known from the mask set and the sites may be very closely spaced, limited only by the diffraction of light.

A method of imaging, i.e. probing, a substrate having microscopic features is by means of condensation figures (CFs) described in a journal article entitled "Imaging of Features on Surfaces by Condensation Figures" by G. Lopez et al. in Science, Apr. 30, 1993, p. 647. The authors describe the formation of an array of tiny droplets on a cold surface having an array of spots which are not wet by the droplets. The spots could be the complex compounds described in the preceding paragraph. The droplets are observed with microscope optics.

Still another bioarray forming technique is described in an article by B. Healey et al. in Science, Aug. 25, 1995 p. 1078. The authors deposited microscopic polymer arrays on a flat substrate by depositing a layer of polymerization solution on a flat plate, such as a glass chip which had been activated for adhesion with the solution. A bundle of fibers was brought into contact with the solution and then backed off and the substrate rinsed. Light was directed into the non-contacted end of the fiber bundle to cause polymer deposition on the substrate below the fibers of the fiber bundle. Polymer spots of a 2.0 micrometer diameter and a spacing of 4.0 micrometers were produced.

Yet another bioarray forming technique is the Southern blotting method in which hybridization is used simultaneously on a large number of DNA segments. DNA is fragmented, electrophoresed, denatured and transferred from a gel to filter paper. Positions of numerous fragments are established. The DNA fragments are robotically moved in accord with the present invention and combined with radioactive phosphorous labelled RNA which can be identified. The degree of DNA-RNA complementation, i.e. probing of the sample, can be determined by autoradiography.

In another bioarray forming technique a polyunsaturated polymerized lipid layer is applied to a support. The lipids have a member of a specific binding pair bound to one end. The lipids have an optical characteristic which is modified upon complexing the other member of the binding pair. Such an optical characteristic can be polarization of light and such light is used to probe the bioarray.

Figure 23:
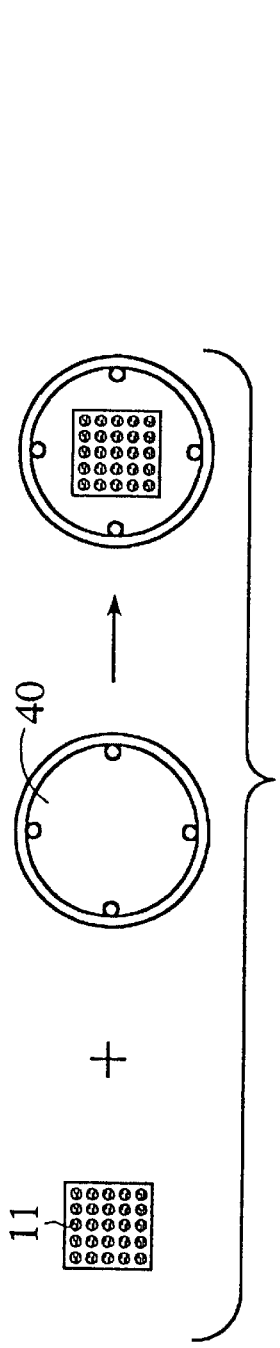
FIG. 23 illustrates a method of affixing a substrate to a manipulator of the present invention.
Figure 24:
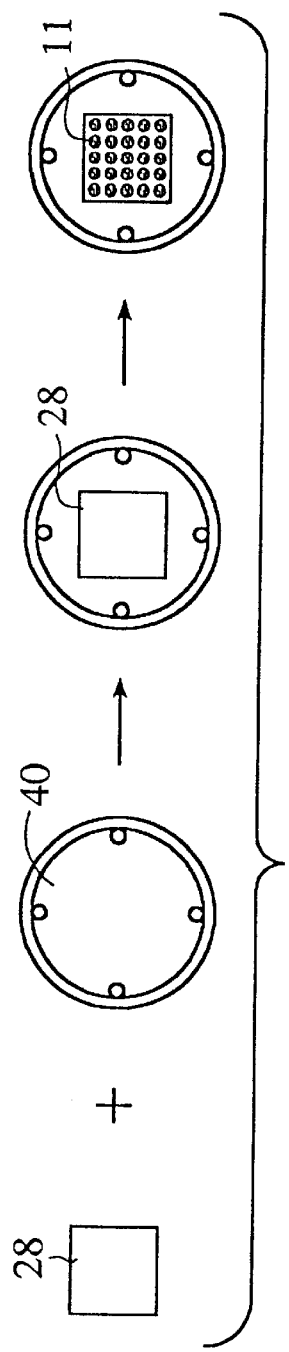
FIG. 24 illustrates a first alternative method of affixing a substrate to a manipulator of the present invention.
Figure 25:
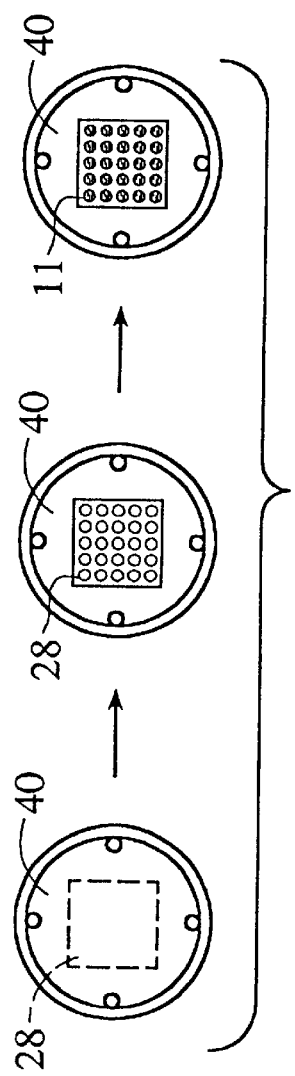
FIG. 25 illustrates a second alternative method of affixing a substrate to a manipulator of the present invention.

In FIG. 23, affixing of bioarray 11 to the flat bottom surface 40 of flat bottom pipette adapter 39, seen in FIGS. 10–12, is given as an example. Specifically, in FIG. 23, a two-dimensional bioarray 11 is preformed and then attached to the flat bottom surface 40 of pipette adapter 39. FIG. 24 presents an alternative wherein the substrate 28 is affixed to flat bottom surface 40 of the pipette adapter, before reactants are caused to become immobilized on the substrate to form the bioarray 11. This alternative works particularly well with the printing type of creation for substrates as discussed with reference to FIGS. 21 and 22. In FIG. 25, it can be seen that the bare substrate 28 may be an integral part of the adapter as fabricated, for instance by injection molding. The substrate 28 is then activated, indicated by shading in FIG. 25, and then the reactants are deposited or otherwise caused to attach to substrate 28.

Although the method of the present invention is designed for detection of target biomolecules in a sample, quantification of the target biomolecules is possible by, for example, recording the sample volume exposed to the substrate, quantifying the degree of complementation at the active sites of the substrate, and calculating the amount of target biomolecule present from these two values. Quantification of the degree of complementation may be performed, e.g., by measuring the percentage of active sites which are fluorescently-labeled or give some other optical signal indicating complementation. Additionally, affixing an excess amount of reactants to the substrate compared to the amount of suspected target biomolecules of the sample is a preferred practice and makes quantification more accurate.

Figure 26:
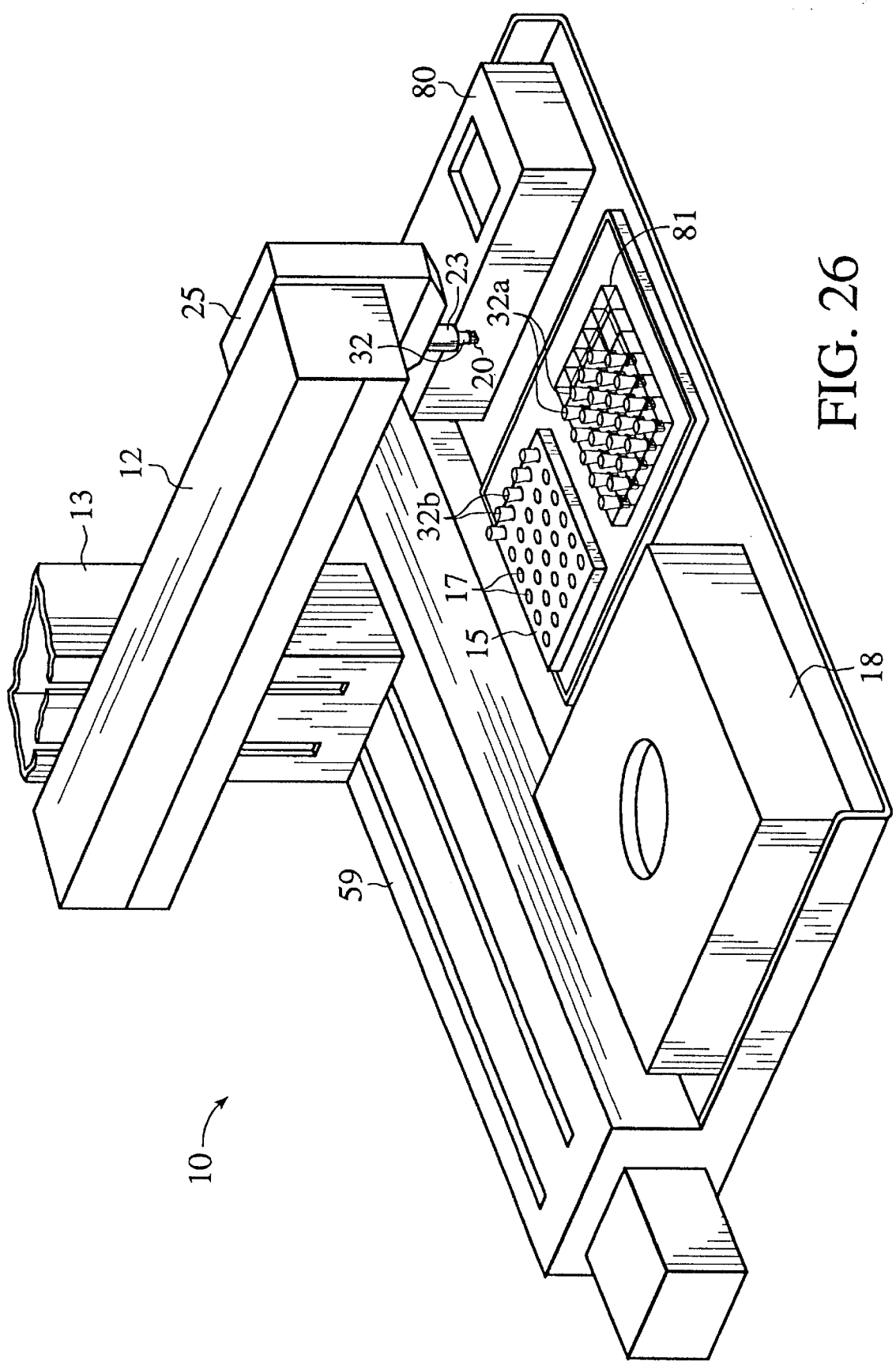
FIG. 26 is a plan perspective view of a version of the instrument of FIG. 1, modified to include a jet-head substrate treating apparatus.

Referring to FIG. 26, an alternate embodiment of instrument 10 of FIG. 1, incorporating the jethead- type reagent dispensing means, is shown. As before, the instrument contains a detection assembly 18 and has a location for placement of the samples. In this case, the samples are within wells 17 of microtiter plate 15. Additionally, FIG. 26 shows a location for a holder 20 for a substrate. For simplicity, pipette adapter 32 has a bioarray held within opposed prongs of a bracket, as illustrated in FIGS. 6–9. Specifically, pipette adapter rack 81 is shown having a plurality of pipette adapters 32a. Here, the instrument also contains a jethead dispensing device 80. The dispensing device is of the type discussed with regard to FIGS. 21 and 22. As with the instrument of FIG. 1, this variation has a robotic arm 12 attached to a tower 13 which, in turn, is attached to a base 59. As before, tower 13 and base 59 have tracks for providing both vertical and horizontal motion to the robotic arm. Additionally, in FIG. 26, the detection assembly 18 and dispensing device 80 are depicted as blocks having holes. These blocks illustrate that the instrument is provided with various stations, each having dedicated operations. The holes enable access to the holder which is attached to the robotic arm.

In operation, the instrument of FIG. 26 provides motion to the bioarray via the robotic arm which picks up a pipette adapter having a substrate support from rack 81, and then moves the pipette adapter into dispensing device 80. Within dispensing device 80, the support may be activated, if necessary, and dispensing or printing of reactants upon the support to create a substrate occurs. Then, robotic arm 12 moves the pipette adapter from dispensing device 80 into contact with a sample, as by placing pipette adapter 32 within a sample well 17 of * microtiter plate 15. The pipette adapters 32b shown in the microtiter plate 15 have been deposited into the wells by robotic arm 12 for interaction of the substrates and the samples. After the appropriate incubation time, robotic arm 12 picks up each pipette adapter and moves it to detection assembly 18 for detection, as before.

In the above description, the robotic arm moved the pipette adapter, with holder and bioarray, to a sample location, such as a microtiter plate. However, the robotic arm could pick up sample in a pipettor and bring it to a stationary holder where the pipettor could dispense the sample onto the holder. Then, the same robotic arm, or another one, with an appropriate gripper could move the holder to a detection station.

The detection station could be any of the optical types described above, but could also be a radioactive tag detector if the immobilized reactants for the target biomolecule had been radioactive. Also, if the tag was a moiety suitable for detection by laser desorption mass spectrometry (LD-MS), then an LD-MS detection system could be used. Other tags and detection systems will be evident to those skilled in the art.

What is claimed is:

1. A holder for bearing a substrate having reactant binding agents for at least one target biomolecule in a sample to form a bound substance having a detectable characteristic for detection of target biomolecules within the sample, the holder comprising:
   a pipette adapter having a bracket with opposed prongs, the opposed prongs bearing the substrate with distinct reactants in a spaced-apart relation, the substrate disposed in a downward-facing orientation,
   wherein the bracket of the pipette adapter is placed on the sample for contact of the sample with the substrate.

2. The holder of claim 1 wherein the pipette adapter has a coupling means for coupling the pipette adapter to a robotic arm.

3. The holder of claim 1 wherein the pipette adapter has a coupling means for coupling the pipette adapter to a hand-held pipette.

4. The holder of claim 1 wherein the bracket of the pipette adapter is sufficiently narrow in diameter to fit within a sample well of a microtiter plate.

5. The holder of claim 1 wherein the bracket prongs of the pipette adapter have knobs positioning the substrate a fixed distance from the sample.

6. The holder of claim 1 wherein the pipette adapter has an evaporation barrier disposed about the pipette adapter.

7. A holder bearing a substrate having an array of reactant binding agents for a plurality of target biomolecules in a sample to form a bound substance having a detectable characteristic for detection of biomolecules within the sample, the holder comprising:
   a pipette adaptor having an end with a flat bottom surface, the flat bottom surface bearing the substrate having an array of reactants in a spaced-apart relation, the substrate being disposed in a downward facing orientation,
   so that, the array of reactants on the substrate can be brought into contact with the sample at the flat bottom surface of the pipette adapter.

8. The holder of claim 7 wherein the pipette adapter has a coupling means for coupling the pipette adapter to a robotic arm.

9. The holder of claim 7 wherein the pipette adapter has a coupling means for coupling the pipette adapter to a hand-held pipettor.

10. The holder of claim 7 wherein the end of the pipette adapter having the flat bottom surface is sufficiently narrow in diameter to fit within a sample well of a microtiter plate.

11. The holder of claim 7 wherein the flat bottom surface of the pipette adapter has knobs positioning the substrate a fixed distance from the sample.

12. The holder of claim 7 wherein the pipette adapter has an evaporation barrier disposed about the pipette adapter.

* * * * *